(12) United States Patent
Pellet et al.

(10) Patent No.: US 6,503,534 B1
(45) Date of Patent: Jan. 7, 2003

(54) PHARMACEUTICAL COMPOSITIONS FOR PROLONGED PEPTIDE RELEASE AND PREPARATION METHOD

(75) Inventors: Marc Pellet, Conde sur Iton; Frederic Bismuth, Dreux, both of (FR)

(73) Assignee: Societe de Conseils de Recherches et d'Applications Scientifiques (S.C.R.A.S.) (FR)

( * ) Notice: Subject to any disclaimer, the term of this patent is extended or adjusted under 35 U.S.C. 154(b) by 0 days.

(21) Appl. No.: 09/646,519

(22) PCT Filed: Mar. 22, 1999

(86) PCT No.: PCT/FR99/00667

§ 371 (c)(1),
(2), (4) Date: Sep. 15, 2000

(87) PCT Pub. No.: WO99/48517

PCT Pub. Date: Sep. 30, 1999

(30) Foreign Application Priority Data

Mar. 25, 1998 (FR) .............................. 98 03667

(51) Int. Cl.⁷ ............................ A61K 9/20; A61K 9/14; A61F 13/00

(52) U.S. Cl. ........................ 424/464; 424/422; 424/484; 424/488

(58) Field of Search ................................ 424/422, 464, 424/484, 488

(56) References Cited

U.S. PATENT DOCUMENTS 5,595,760 A    1/1997   Cherif-Cheikh ............. 424/464

FOREIGN PATENT DOCUMENTS

WO            9013285      11/1990

*Primary Examiner*—Shelley A. Dodson
(74) *Attorney, Agent, or Firm*—Bierman, Muserlian and Lucas

(57) ABSTRACT

Solid or semisolid pharmaceutical composition comprising a gellable and water-soluble peptide salt optionally combined with an appropriate excipient, said pharmaceutical composition being characterized in that the peptide salt has a high specific surface area and in that, once injected into a patient, it forms a gel in contact with this patient's body substances, said gel being capable of releasing the peptide over a prolonged period of at least 15 days.

14 Claims, No Drawings

PHARMACEUTICAL COMPOSITIONS FOR PROLONGED PEPTIDE RELEASE AND PREPARATION METHOD

This application is a 371 of PCT/FR99/00667 filed Mar. 22, 1999.

The invention relates to new pharmaceutical compositions intended for the sustained release of peptides and to the process for their preparation. U.S. Pat. No. 5,595,760 has already described solid and semisolid pharmaceutical compositions intended for the sustained release of peptides, which are composed of a gellable and water-soluble peptide salt optionally combined with an appropriate monomeric excipient. After administration to a patient, these compositions gel and allow a sustained release over a period of at least three days.

These compositions brought a considerable advantage compared with the prior art in terms of the simplicity of their manufacture and use.

The Applicant has now discovered, unexpectedly, that improved compositions can be obtained which, while utilizing the same principle, make it possible to obtain a slower release than the conventional compositions, it being possible for said release to extend over one, two, three months or more in some cases. In particular, the initial peak (or burst) is reduced.

Furthermore, the compositions of the invention are easier to prepare. In particular, the peptide grinding time and the force required for mixing can be greatly reduced. Also, the characteristics of the compositions of the invention are more homogeneous.

Apart from the advantages mentioned above, for the same amount of peptide, some of these compositions have the advantage of requiring a smaller injection force, so they are more convenient to use. This therefore makes it possible to use syringes with a smaller needle diameter than that which would be necessary for the equivalent compositions of the prior art.

It is found moreover that these compositions give very good results in the in vivo tests and that the individual experimental deviations are reduced, making it possible to treat a greater proportion of patients effectively.

All these advantages are obtained by giving the peptide a higher specific surface area than that of the non-matrix (gellable) compositions known a person skilled in the art and described in the U.S. Pat. No. 5,595,760. The gellable compositions according to the invention preferably use peptides whose specific surface area has been increased to at least 4 $m^2/g$, and more preferably to 8 $m^2/g$ or more, this characteristic giving them a slower and more regular release profile. The compositions according to the invention are obtained by using a special lyophilization process comprising a flash-freezing phase of a peptide solution, said process being described below.

The invention therefore relates first and foremost to a solid or semisolid pharmaceutical composition comprising a gellable and soluble peptide salt optionally combined with an appropriate excipient, said pharmaceutical composition being characterized in that the peptide salt has a high specific surface area and in that, once injected into a patient, it forms a gel in contact with this patient's body substances, said gel being capable of releasing the peptide over a prolonged period of at least 15 days.

High specific surface area is understood as meaning a specific surface area greater than that which would be obtained by a lyophilization involving the slow freezing of a solution of a peptide salt. Slow freezing is understood as meaning a freezing which is not a flash freezing as describe hereafter or in the PCT Patent Application WO 98/47489.

Preferably, the peptide salt has a specific surface area of at least 8 $m^2/g$ and, once injected into a patient, it forms a gel in contact with this patient's body substances, said gel being capable of releasing the peptide over a prolonged period of at least 15 days.

The invention therefore preferably relates to a solid or semisolid pharmaceutical composition comprising a gellable and soluble peptide salt optionally combined with an appropriate excipient, said pharmaceutical composition being characterized in that the peptide salt has a specific surface area of at least 4 or 5 $m^2/g$, preferably 8 $m^2/g$, and in that, once injected into a patient, it forms a gel in contact with this patient's body substances, said gel being capable of releasing the peptide over a prolonged period of at least 15 days.

Peptide is understood as meaning either a peptide or a protein. The peptide salts which can be used for the invention may be selected in particular from a group comprising the salts of the following substances: triptorelin, lanreotide, octreotide (as described for example in Patent EP 29,579), a compound with LH–RH activity, such as triptorelin, goserelin, leuprorelin or buserelin, an LH—RH antagonist, a GPIIb/IIIa antagonist, a compound with a similar activity to a GPIIb/IIIa antagonist, erythropoietin (EPO) or one of its analogues, the various types of interferon-$\alpha$, interferon-$\beta$ or -$\gamma$, somatostatin, a somatostatin derivative such as that described in the European Patent EP 215,171, a somatostatin analogue such as that described in the U.S. Pat. No. 5,552,520 (this patent itself includes a list of other patents describing somatostatin analogues, which are incorporated in the present application by way of reference), insulin, a growth hormone (GH), a growth hormone releasing factor (GHRF), a growth hormone releasing peptide (GHRP), an epidermal growth factor (EGF), a melanocyte stimulating hormone (MSH), a thyrotropin releasing hormone (TRH) or one of its derivatives, a thyroid stimulating hormone (TSH), a luteinizing hormone (LH), a follicle stimulating hormone (FSH), a parathyroid hormone (PTH) or one of its derivatives, a lysozyme hydrochloride, a parathyroid hormone related peptide (PTHrp), an N-terminal peptide fragment (position 1→34) of human PTH, vasopressin or one of its derivatives, oxytocin, calcitonin, a calcitonin derivative with a similar activity to that of calcitonin, a calcitonin gene related peptide (CGRP), glucagon, a peptide similar to glucagon (GLP), gastrin, a gastrin releasing peptide (GRP), secretin, pancreozymin, cholecystokinin, angiotensin, human placental lactogen, human chorionic gonadotropin (HCG), enkephalin, an enkephalin derivative, colony stimulating factor (CSF), endorphin, kyotorphin, interleukins, for example interleukin-2, tuftsin, thymopoietin, thymostimulin, thymic humoral factor (THF), thymic serum factor (TSF), a derivative of thymic serum factor (TSF), thymosin, thymic factor X, tumour necrosis factor (TNF), motilin, bombesin or one of its derivatives, such as those described in the U.S. Pat. No. 5,552,520 (this patent itself includes a list of other patents describing bombesin derivatives, which are incorporated in the present application by way of reference), prolactin, neurotensin, dynorphin, caerulein, substance P, urokinase, asparaginase, bradykinin, kallikrein, nerve growth factor, a blood clotting factor, polymixin B, colistin, gramicidin, bacitracin, a protein synthesis stimulating peptide, an endothelin antagonist or one of its derivatives, a vasoactive intestinal polypeptide (VIP), adrenocorticotropic hormone (ACTH) or one of its fragments, a platelet derived growth factor (PDGF), a bone morphogenetic protein (BMP), a pituitary adenylate cyclase activating polypeptide (PACAP), neuropeptide Y (NPY), peptide YY (PYY) and a gastric inhibitory polypeptide (GIP). Any water-soluble peptide or protein salt may also be used by a person skilled in the art if they consider it appropriate.

The peptide salt used for the invention will preferably be selected from a group comprising salts of somatostatin or its analogues, particularly lanreotide acetate or octreotide acetate, triptorelin salts, particularly triptorelin acetate, salts of calcitonin or its analogues, salts of LH—RH hormone analogues, salts of GH, GHRF, PTH or PTHrp peptide, and analogues of the latter.

The peptide salts which can be used for the invention are preferably pharmaceutically acceptable salts of organic acids, such as those of acetic, lactic, malic, ascorbic, succinic, benzoic, methanesulphonic or toluenesulphonic acids, or pharmaceutically cceptable salts of inorganic acids, such as those of hydrochloric, hydrobromic, hydriodic, sulphuric or phosphoric acids. In particular, they can be acetates of said peptide. However, the solubility of the peptide salt must be fairly high in order to allow the freezing of the peptide salt with a small amount of solvent.

Preferably, the specific surface area of the peptide salt will be at least 4 or 5 $m^2/g$. More preferably, the peptide salt will have a specific surface area of at least 10 or 15 $m^2/g$. Particularly preferably, the peptide salt will have a specific surface area of at least 20 $m^2/g$ or even 30 $m^2/g$. These specific surface areas can be obtained using the processes described below or in PCT Patent Application WO 98/47489.

Said solid or semisolid composition may comprise from 0 to 30% of an excipient. Excipients which can be used for the invention are pharmaceutically acceptable excipients which facilitate the preparation of the compositions of the invention and/or their administration. The chosen excipients will have to be water-soluble and biodegradable in contact with the body substances. Notable possibilities are polyalcohols such as mannitol and sorbitol, sugars such as glucose and lactose, surfactants, organic solvents or polysaccharides. However, these excipients will not be matrix polymers such as polymers of the PLGA type.

The process which will be used to prepare the pharmaceutical compositions of the invention is characterized in that it involves a lyophilization step comprising the rapid immersion of a dilute solution of the peptide salt in a medium whose temperature is below −50° C.

Rapid immersion must be understood as meaning contact with a low temperature medium, causing instantaneous freezing of the solution of water-soluble substance.

Dilute solution of the peptide salt is understood as meaning a solution whose concentration of said peptide salt is less than half the saturation concentration and preferably less than a quarter of said saturation concentration when the latter is at least 200 g/l. The peptide salt which can be obtained by this process has a high specific surface area.

For the lyophilization, the solution may be frozen for example in a tray floating in a tank of liquid nitrogen, before the actual lyophilization is carried out.

Preferably, the rapid immersion will be carried out by pouring a dilute solution of the peptide salt onto a metal plate at very low temperature. The temperature of the plate will preferably be below −70° C. and more preferably below −80° C. or even −120° C. The peptide salt which can be obtained by this immersion has a very high specific surface area, as described above.

More preferably, in order to obtain the maximum specific surface area, the rapid immersion of the solution will be preceded by a micronization of the solution of active substance.

If a specific surface area greater than 10 $m^2/g$ is required, the process which includes a micronization step will preferably be employed. The specific surface area obtained for the active substance after lyophilization will preferably be greater than 15 $m^2/g$. This specific surface area will even more preferably be greater than 20 $m^2/g$ or even 30 $m^2/g$. The high specific surface areas will be particularly useful because the force required for injection will be lower and it will be possible for the needle used for the injection to have a smaller diameter.

For example, to obtain a very high specific surface area, it may be chosen to atomize the solution by spraying it through an atomizer onto a plate at very low temperature. The temperature of the plate will be below −50° C., preferably below −70° C. and more preferably below −80° C. or even −120° C. This temperature may be reached for example by immersing the metal plate in a very low temperature medium, for example liquid nitrogen. In one preferred variant of the invention, the metal plate is hollow and the solution is sprayed inside said plate by means of an atomizer.

Other freezing techniques can be considered for obtaining a very high specific surface area, for example atomization of the solution of active substance into a precooled bath of a non-solvent for the peptide salt. The non-solvent will preferably be a liquefied gas, for example liquid nitrogen.

Another possibility is to freeze the solution of peptide salt on a cooled rotating tray (drum freezing). As indicated previously, this freezing will preferably be preceded by a micronization of the solution of peptide salt.

The specific surface area of the active substance is a favourable factor for obtaining release over a prolonged period. In fact, particles of a peptide salt which have the same size but different specific surface areas will give totally different results.

To vary the specific surface areas obtained, the freezing conditions of the solution of active substance may be varied by modifying different parameters, such as, for example the freezing rate or the concentration of the solution.

The lyophilization will be carried out under conventional conditions known to a person skilled in the art. When the lyophilization is complete, the peptide salt is incorporated, optionally with an excipient, into a solid or semisolid pharmaceutical composition as described above. This solid or semisolid composition can be mixed with water as described in the U.S. Pat. No. 5,595,760, taking particular account of the fact that the water can be present in an amount which is less than 50% of the amount needed to dissolve the peptide salt completely, it also being necessary to adapt said amount so as to give said composition a semisolid consistency.

Preferably, where possible, the amount of water added will be less than 30% and more preferably less than 10% of the amount needed to dissolve the peptide salt completely.

The proportion of peptide in the compositions according to the invention will be determined by the release time which it is desired to achieve, but it cannot exceed a maximum value corresponding to the limiting concentration at which the solid or semisolid composition can be injected with a syringe fitted with a needle of customary diameter. The specific surface area of the peptide may be varied in order to increase said limiting concentration, if necessary; the higher the specific surface area of the peptide, the lower will be the injection force, making it possible to reduce the diameter of the needle required for injection.

For example, for lanreotide acetate with a high specific surface area (for example of at least 4 $m^2/g$) obtained by a lyophilization process involving a flash-freezing step, it will be possible to use semisolid compositions with concentrations of 25 or 30% by weight of lanreotide acetate in water (i.e. 20.5 or 24.6% by weight of pure lanreotide). Such compositions may easily be injected with needles having an internal diameter of the order of 1 mm and a length of the order of 32 mm.

Preferably, the compositions of the invention based on lanreotide acetate will comprise from 20 to 35% and more preferably from 25 to 30% by weight of lanreotide acetate.

The mixing of the solid composition and water to give semisolid compositions is preferably carried out in a device consisting of two interconnected syringes. For example, the peptide salt is introduced into one of the syringes, which is then evacuated, the water is introduced into the other syringe and the mixture is homogenized by the reciprocating movement of the two pistons. In this connection, a person skilled in the art may also usefully consult PCT Patent Application WO 97/46202.

As indicated above, the semisolid compositions according to the invention are preferably used in the pharmaceutical field. The compositions according to the invention may be injected into a patient, for example, by using. the devices described in U.S. Pat. No. 5,595,760.

Once injected into a patient, the semisolid compositions according to the invention form a gel in contact with this patient's body substances, said gel being capable of releasing the peptide over a prolonged period of at least 15 days. The release period will preferably be at least 1 month and more preferably 2 or even 3 months.

Unless defined otherwise, all the technical and scientific terms used here have the same meanings as those commonly understood by an ordinary specialist in the field to which this invention belongs. Likewise, all the publications, patent applications, patents and other references mentioned here are incorporated by way of reference.

The following examples are given in order to illustrate the above procedures and must not under any circumstances be considered as limiting the scope of the invention.

EXAMPLES

Methods

Measurement of the specific surface area

For all the following examples, the specific surface area of the peptide salt was determined by the so-called B.E.T method (absorption of a nitrogen monolayer on the active substance), a method well known to a person skilled in the art.

Mixing of the peptide and the water

For all the following examples, the peptide salt and the water are mixed in a device consisting of two interconnected 50 ml syringes. The peptide salt is introduced into one of the syringes, which is then evacuated, the water is introduced into the other syringe and the mixture is homogenized by the reciprocating movement of the two pistons.

Example 1

Lanreotide acetate with a specific surface area of 0.61 $m^2/g$ is dissolved in water to a concentration of 30 g/l and is frozen by pouring the aqueous solution obtained into a hollow metal tray cooled on the outside by liquid nitrogen. This freezes the peptide salt. Lyophilization is then carried out and lanreotide acetate with a specific surface area of 5.41 $m^2/g$ is recovered. 3 g of lanreotide acetate obtained in this way are mixed with 6.927 ml of water to give a semisolid paste. The mixture is then mixed as indicated above to give 10.927 g of a compact, homogeneous, semisolid composition. This composition can be used directly for injection into the subject to be treated.

Example 2

9.0 g of lanreotide acetate with a specific surface area of 1.73 $m^2/g$ are dissolved in 300 ml of water. This solution is then sprayed with an atomizer into a hollow metal tray, the bottom of which is immersed in liquid nitrogen. This freezes the peptide salt. Lyophilization is then carried out and 8.7 g of lanreotide acetate with a specific surface area of 28.2 $m^2/g$ are recovered. 3 g of lanreotide acetate obtained in this way are mixed with 7.183 ml of water to give a semisolid paste. The mixture is then mixed as indicated above to give 10.183 g of a compact, homogeneous, semisolid composition. This composition can be used directly for injection into the subject to be treated.

Examples 3 and 4

The same protocol is used for these two examples:

5 g of lanreotide acetate are dissolved in sterile water to give a solution of the chosen concentration. This solution is atomized with a 500 ml sprayer whose jet is adjusted so as to give the finest possible droplets. The droplets obtained are sprayed into a tray, the bottom of which is immersed in liquid nitrogen. Two temperature probes are introduced into the tray beforehand so that the change in the temperature of the product can be monitored.

Once the product is frozen, the tray is introduced into a lyophilizer whose plate is at about −54° C.

The temperature of the products and that of the plate are left to equilibrate for 1 hour. This leads on to the sublimation phase (the temperature of the plate is then set at 20° C. and the pressure in the tank at 100 $\mu$bar). This phase lasts for about 30 hours. The mean final temperature of the product is about 13° C. The secondary desiccation which follows (pressure reduced to 50 $\mu$bar in the tank) lasts for about 24 hours. The mean final temperature of the product is 20° C.

The characteristics of the reagents used and the products obtained are summarized in the tables below

| Characteristics | Example 3 | Example 4 |
| --- | --- | --- |
| Weight of lanreotide acetate used (g) | 5.00 | 5.00 |
| Concentration of the solution (g/l) | 30 | 10 |
| Weight of lanreotide acetate recovered (g) | 4.54 | 4.10 |
| Specific surface area obtained ($m^2/g$) | 36 | 43 |

Like the lanreotide acetate of Examples 1 and 2, the lanreotide acetate of Examples 3 and 4 can be incorporated into semisolid pharmaceutical compositions simply by being mixed with an appropriate amount of water.

Study of the properties of compositions according to the invention

Three tests were performed. The first concerns the force required to inject a dose of the composition obtained according to Example 2, the second concerns the in vitro release profile of the same composition and the third concerns the release profile of the compositions of Examples 1 and 2 in dogs, compared with that obtained for a composition which is analogous but contains a peptide of low specific surface area.

Reference

A composition prepared according to the following protocol was chosen to serve as a reference for the injection force measurement and the in vitro test: Lanreotide acetate is dissolved in water to give a solution with a concentration of 30 g4, which is poured into a hollow tray immersed in liquid nitrogen beforehand. The frozen lanreotide acetate is then lyophilized and incorporated into a solid composition as described in Example 2 above, 6.817 ml of water being added to 3 g of lanreotide acetate to give 9.817 g of semisolid composition.

Measurement of the force required for injection

A dynamometer is used to measure the force to be applied to the piston of the syringe in order to move it forward, relative to the displacement of the piston (amount of semisolid composition injected: about 280 mg; as in Example 2, the reference contains about 0.25 mg of lanreotide acetate per mg of semisolid composition). By expressing the displacement of the piston in mm as a function of the applied force in N, a three-phase profile is obtained from which 8 noteworthy values are taken and used to calculate a mean value for the force required for injection. The value recorded for each test is the mean of 5 measurements made on the same composition.

In vitro release profile

In order to obtain meaningful results, each composition tested is divided into 6 samples and the mean of the 6 samples is recorded. In each case, the semisolid composition to be tested is placed in a cylindrical dialysis tube equipped with a semipermeable synthetic membrane. Both ends of the tube are closed. This tube is placed in 20 ml of 0.9% aqueous NaCl solution, the temperature being set at 37° C. The medium is stirred (magnetic stirrer). Half an hour, 1 hour, 2 hours 3 hours, 4 hours, 24 hours, 48 hours and 72 hours after the start of the test, samples of the NaCl solution are taken and the lanreotide content is determined by UV analysis (wavelength: 280 nm). At the end of the test (after 96 hours for the reference), the residual amount of peptide contained in the dialysis tube is determined so that the results can be expressed as the proportion of peptide released relative to the total initial amount.

Results

The results obtained are summarized in Table I below:

TABLE I

| Parameters measured | Reference | Example 2 |
|---|---|---|
| Amount of lanreotide in 1 mg of gel (in mg) | 0.252 | 0.250 |
| Specific surface area of the lanreotide acetate incorporated (m$^2$/g) | 3.64 | 28.6 |
| Force required for injection (N) | 41.0 | 27.3 |
| Proportion dissolved after 0.5 h | 1.5 | 1.0 |
| Proportion dissolved after 1 h | 2.7 | 2.1 |
| Proportion dissolved after 2 h | 5.1 | 4.0 |
| Proportion dissolved after 3 h | 7.2 | 6.1 |
| Proportion dissolved after 4 h | 9.5 | 8.0 |
| Proportion dissolved after 24 h | 39.3 | 29.9 |
| Proportion dissolved after 48 h | 62.6 | 38.8 |
| Proportion dissolved after 72 h | 77.5 | 44.7 |
| Proportion dissolved after 96 h | 88.4 | 50.3 |

Additional measurements were made for Example 2 and show dissolved proportions of 57.7% after 144 hours, 66.8% after 216 hours and 77.7% after 334 hours.

It is therefore seen that the composition of Example 2, which differs from the reference composition by having almost 10 times the specific surface area, releases the peptide considerably more slowly than the reference composition. Furthermore, the composition of Example 2 requires a smaller injection force than the reference composition.

In vivo release profile in does

The reference composition for this test contains 30% by weight of lanreotide acetate with a specific surface area of 0.8 m$^2$/g (obtained by a lyophilization process involving slow freezing), the remainder of the composition consisting of water. The concentration of pure lanreotide in the reference composition and the composition of Example 2 is therefore 246 mg per gram of composition.

The tests are performed on two groups of 6 beagle dogs, each dog receiving an intramuscular injection of 60 mg of reference composition or composition of Example 2.

Results

The plasma concentrations measured for Examples 1 and 2 (expressed in ng/ml) are respectively reported in Table II below:

TABLE II

| Time | Ref. | Mean | Ex. 2 |
|---|---|---|---|
| 0 | 0.000 | 0.000 | 0.000 |
| 0.083 h | 4.909 | 4.365 | 3.642 |
| 0.25 h | 20.930 | 11.348 | 14.591 |
| 0.5 h | 32.215 | 22.711 | 17.637 |
| 1 h | 43.215 | 26.863 | 24.847 |
| 2 h | 45.208 | 32.831 | 29.262 |
| 4 h | 44.129 | 30.112 | 29.696 |
| 8 h | 58.362 | 30.218 | 26.713 |
| 12 h | 48.041 | 20.831 | 18.235 |
| 1 day | 29.462 | 20.771 | 16.977 |
| 2 days | 13.677 | 7.731 | 13.105 |
| 3 days | 9.974 | 8.000 | 12.248 |
| 4 days | 6.683 | 6.716 | 6.520 |
| 8 days | 3.583 | 2.564 | 3.179 |
| 11 days | 3.225 | 2.305 | 2.513 |
| 15 days | 1.786 | 2.280 | 2.075 |
| 18 days | 1.305 | 2.553 | 1.481 |
| 22 days | 1.329 | 2.317 | 1.097 |
| 25 days | 1.182 | 1.582 | 1.605 |
| 29 days | 1.024 | 0.983 | 0.951 |
| 32 days | 0.685 | 0.696 | 9.924 |
| 36 days | 0.362 | 0.486 | 0.714 |
| 39 days | 0.194 | 0.521 | 0.792 |
| 43 days | 0.217 | 0.443 | 0.715 |
| 46 days | 0.189 | 0.332 | 0.768 |
| 50 days | 0.153 | 0.337 | 0.511 |
| 53 days | 0.148 | 0.297 | 0.513 |
| 57 days | 0.150 | 0.228 | 0.466 |
| 60 days | 0.131 | 0.254 | 0.411 |
| 65 days | 0.094 | 0.191 | 0.281 |
| 72 days | 0.093 | 0.120 | 0.312 |
| 79 days | 0.044 | 0.147 | 0.157 |
| 86 days | 0.063 | 0.068 | 0.200 |
| 93 days | 0.050 | 0.072 | 0.167 |
| 100 days | 0.046 | 0.052 | 0.137 |
| 107 days | 0.000 | 0.064 | 0.107 |
| 114 days | 0.000 | 0.057 | 0.062 |
| 122 days | 0.000 | 0.034 | 0.067 |
| 128 days | 0.000 | 0.030 | 0.048 |
| 135 days | 0.000 | — | 0.000 |

These in vivo tests confirm that the initial peak (or burst) is considerably reduced for the compositions of Examples 1 and 2 compared with an analogous composition containing a peptide of lower specific surface area. Furthermore, the release becomes too low after 60 days for the reference composition, whereas for the compositions of Examples 1 and 2 it is sufficient to ensure a plasma level in excess of 0.1 ng/ml for at least 79 days and 107 days respectively.

What is claimed is:

1. A solid or semi-solid pharmaceutical composition comprising a gellable and water-soluble peptide salt and optionally an appropriate excipient, the peptide salt having a high specific surface area of at least about 4 m$^2$/g and when injected into a patient, forming a gel in contact with the body substances whereby the peptide is released over a period of at least 15 days.

2. The composition of claim 1 wherein the peptide is released over a period of at least one month.

3. The composition of claim 1 wherein the peptide is released over a period of at least 3 months.

4. The composition of claim 1 wherein the peptide salt has a specific surface area of at least 8 m$^2$/g.

5. The composition of claim 1 wherein the peptide salt has a specific surface area of at least 20 m$^2$g.

6. The composition of claim 1 wherein the peptide salt has a specific surface area of at least 30 m$^2$/g.

7. The composition of claim 1 wherein an excipient is present up to 30% by weight of the composition.

8. The composition of claim 1 wherein the excipient is at least one member selected from the group consisting of polyalcohols, sugars, surfactants, organic solvents and polysaccharides.

9. The composition of claim 1 also containing water in an amount less than 50% of the amount needed to completely dissolve the peptide salt and adapted to give the composition a semi-solid consistency.

10. Pharmaceutical composition according to claim 1, characterized in that the peptide salt is selected from the salts of the following substances: triptorelin, lanreotide, octreotide, a compound with LH—RH activity, such as triptorelin, goserelin, leuprorelin or buserelin, an LH—RH antagonist, a GPIIb/IIIa antagonist, a compound with a similar activity to a GPIIb/IIIa antagonist, erythropoietin (EPO) or one of its analogues, the various types of interferon-α, interferon-β or γ, somatostatin, a somatostatin derivative, a somatostatin analogue, insulin, a growth hormone (GH), a growth hormone releasing factor (GHRF), a growth hormone releasing peptide (GHRP), an epidermal growth factor (EGF), a melanocyte stimulating hormone (MSH), a thyrotropin releasing hormone (TRH) or one of its derivatives, a thyroid stimulating hormone (TSH), a luteinizing hormone (LH), a follicle stimulating hormone (FSH), a parathyroid hormone (PTH) or one of its derivatives, a lysozyme hydrochloride, a parathyroid hormone related peptide (PTHrp), an N-terminal peptide fragment (position 1 →34) of human PTH, vasopressin or one of its derivatives, oxytocin, calcitonin, a calcitonin derivative with a similar activity to that of calcitonin, a calcitonin gene related peptide (CGRP), glucagon, a peptide similar to glucagon (GLP), gastrin, a gastrin releasing peptide (GRP), secretin, pancreozymin, cholecystokinin, angiotensin, human placental lactogen, human chorionic gonadotropin (HCG), enkephalin, an enkephalin derivative, colony stimulating factor (CSF), endorphin, kyotorphin, interleukins, for example interleukin-2, tuftsin, thymopoietin, thymostimulin, thymic humoral factor (THF), thymic serum factor (TSF), a derivative of thymic serum factor (TSF), thymosin, thymic factor X, tumour necrosis factor (TNF), motilin, bombesin or one of its derivatives, prolactin, neurotensin, dynorphin, caerulein, substance P, urokinase, asparaginase, bradykinin, kallikrein, nerve growth factor, a blood clotting factor, polymixin B, colistin, gramicidin, bacitracin, a protein synthesis stimulating peptide, an endothelin antagonist or one of its derivatives, a vasoactive intestinal polypeptide (VIP), adrenocorticotropic hormone (ACTH) or one of its fragments, a platelet derived growth factor (PDGF), a bone morphogenetic protein (BMP), a pituitary adenylate cyclase activating polypeptide (PACAP), neuropeptide Y (NPY), peptide YY (PYY) and a gastric inhibitory polypeptide (GIP).

11. Pharmaceutical composition according to claim 10, characterized in that the peptide is selected from the group consisting of salts of somatostatin or its analogues, triptorelin salts, salts of calcitonin or its analogues, salts of LH—RH hormone analogues, salts of GH, GHRF, PTH hormones or PTHrp peptide, and analogues of the latter.

12. Pharmaceutical composition according to claim 10, characterized in that the peptide is triptorelin acetate.

13. Pharmaceutical composition according to claim 11, characterized in that the peptide is triptorelin acetate.

14. Pharmaceutical composition according to claim 11, characterized in that the peptide is lanreotide acetate.

* * * * *